United States Patent [19]

Linkie et al.

[11] Patent Number: 4,747,825
[45] Date of Patent: May 31, 1988

[54] APPARATUS AND METHODOLOGY FOR PULSED ADMINISTRATION OF GROWTH PROMOTING AGENTS

[75] Inventors: Daniel M. Linkie, Suffern, N.Y.; Michael O. Thorner, Charlottesville, Va.

[73] Assignee: Ferring Laboratories, Inc., Suffern, N.Y.

[21] Appl. No.: 626,400

[22] Filed: Jun. 29, 1984

[51] Int. Cl.$^4$ ............................................. A61M 31/00
[52] U.S. Cl. ...................................... 604/51; 604/49; 604/151; 424/468; 514/12
[58] Field of Search ................... 604/51, 49, 151, 890, 604/891

[56] References Cited

U.S. PATENT DOCUMENTS

| | | | |
|---|---|---|---|
| 3,498,228 | 3/1970 | Blumle et al. | 604/151 |
| 3,559,644 | 2/1971 | Stoft et al. | 604/151 |
| 3,809,871 | 5/1974 | Howard et al. | 604/49 |
| 4,306,553 | 12/1981 | Dorman et al. | 604/49 |
| 4,313,439 | 2/1982 | Bobb et al. | 604/51 |
| 4,342,312 | 8/1982 | Whitney et al. | 604/51 |
| 4,397,639 | 8/1983 | Eschweiler et al. | 604/153 |
| 4,517,181 | 5/1985 | Ling et al. | 514/12 |
| 4,529,595 | 7/1985 | River et al. | 514/12 |

Primary Examiner—William R. Dixon, Jr.
Assistant Examiner—Margaret B. Medley
Attorney, Agent, or Firm—Hopgood, Calimafde, Kalil, Blaustein & Judlowe

[57] ABSTRACT

A method and apparatus for therapeutically effective treatment of a living animal comprising administering a dynamic dosage of growth hormone releasing factor or analog thereof, or administering growth hormone or analogs thereof in a chronic course of treatment in a subdesensitizing regimen. Also a method of diagnosing living animals with an anterior pituitary unresponsive to growth hormone releasing factor or analogs thereof. A method of determining the optimum GRF and GH dynamic dosage for a given living animal, particularly a human.

30 Claims, 1 Drawing Sheet

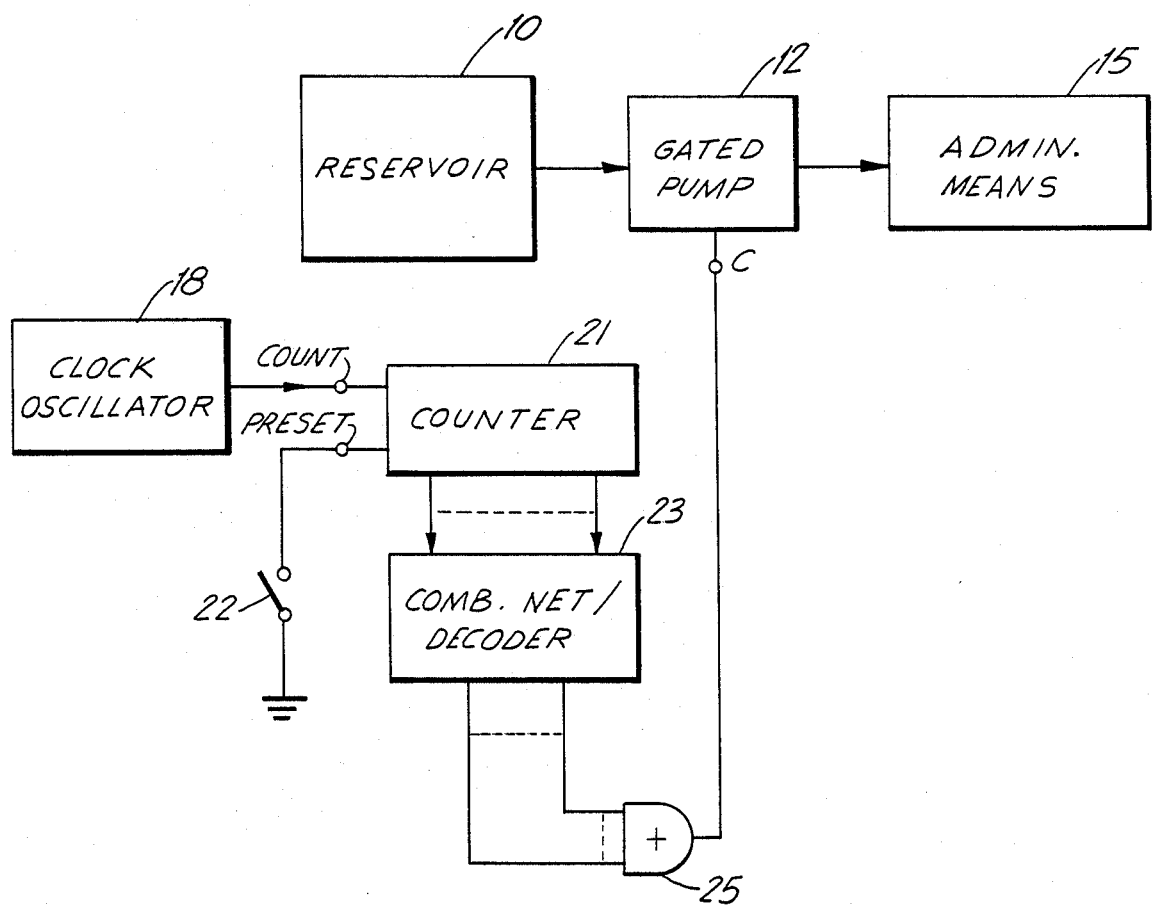

APPARATUS AND METHODOLOGY FOR PULSED ADMINISTRATION OF GROWTH PROMOTING AGENTS

BACKGROUND OF THE INVENTION

Therapeutic administration of hormones—drugs that act at sites distant from locus of release—has been subject to the technical limitations of the pharmacological art. In general, pharmacological administration of hormones has meant virtually instant introduction of a large dose of an active agent. This is clearly contrary to physiological nature of release which is in low doses released as required by particular organism.

The dichotomy between pharmacology and physiology is commonly noted in insulin use. Normal subjects release insulin as needed. High amounts may be released when food is eaten, but chronic low levels remain available in time of less, but not negligible, demand. Diabetic subjects receive an approximated insulin dosage in about 1 to 3 injections daily with only minimal accommodation possible for moment to moment insulin demands.

A similar problem presents itself with the administration of Growth Hormone Releasing Factor (GRF) and Growth Hormone (GH).

It is believed that GRF is most effective when administered in a non-desensitizing manner and over a length of time. The GH secreting cells must be stimulated by GRF which stimulation may be effected by chronic pulsatile administration of GRF. GRF is a hormone produced in the brains of animals which stimulates the release of GH from the brain. In humans, GRF is believed to be produced in the hypothalamus, stimulating release of GH by the anterior pituitary. Studies have indicated that continuous exposure of GH releasing cells to GRF desensitizes those cells, reducing the release of GH in response to a particular dose of GRF. GH is believed to similarly desensitize its effector sites upon chronic administration.

It is an object of this invention to provide a method and apparatus to utilize GRF or GH to promote growth.

It is a further object of this invention to provide a method of treating GRF and GH deficiencies in subjects suffering from such deficiencies.

It is another object of this invention to furnish a method of diagnosis suitable to identify those subjects suffering from the inability of the pituitary to respond to dynamic dosage of GRF.

SUMMARY OF THE INVENTION

It has now been discovered that to be effectively utilized GRF or GH should be administered in a subdesensitizing dosage regimen of that frequency of dosage and amount of dosage and duration of dosage that will maintain highly effective response to the hormone introduced. To be chronically effective such dosage must be maintained at nondesensitizing level for weeks, months and even years, all the while maintaining an effective level.

The range of dosage that is both subdesensitizing and chronically effective may be termed "dynamic dosage". Dynamic dosage then is maintained over time at the low dosage end to avoid ineffectiveness of hormone treatment by not having enough hormone present often enough and at the high dosage end to avoid desensitizing the receptor systems.

Human Growth Hormone Releasing Factor has been variously identified. This identification is complicated by the small amounts present in tissue and by the effectiveness of its many analogues.

As used herein, the material known as Human Pancreatic Tumor Growth Hormone Releasing Factor (hpGRF) with from 44 to 40 amino acid units describes the generally accepted composition of GRF. The formula of hpGRF is as follows:

H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$. Analogs are the peptide hpGRF (1–40) and the peptide hpGRF (1–37) which are shorter at the C-terminal by 4 and 7 residues respectively. Growth hormone releasing factors as used here include those of other animal species that are polypeptides which have sequence homologies with hpGRF. These are generically referred to by the name "GRF" and include biologically active fragments of these peptides, as well as analogs and derivatives of any of the foregoing for all species.

The structure of Growth Hormone has been defined by researchers in the art and growth hormone and its analogs and polypeptides which have sequence homologies with it and biologically active fragments of these peptides will, as well as analogs and derivatives as any of the foregoing for all species, be referred to as GH.

BRIEF DESCRIPTION OF THE DRAWING

The FIGURE is a schematic drawing for pulsed administration of growth promoting agents.

DETAILED DESCRIPTION OF THE INVENTION

The following detailed description of the invention will indicate a method of treating subjects with GRF and GH to permit growth and the method of using GRF and GH. This also constitutes a method of treating subjects with growth deficiencies of GRF or GH etiology, and a method of diagnosing those subjects whose growth retardation is due to the inability of the pituitary to respond to dynamic dosage of GRF.

The invention is predicated upon a desire to introduce GRF and GH in a physiologically mimetic fashion as can be seen from the following data.

In vitro experiments indicate that live pituitary cell preparations presented with GRF rapidly become desensitized to increased GRF dosages.

Further, hpGRF-40 and hpGRF-44 are probably identical with the human hypothalamic growth hormone releasing hormone(s). In normal men hpGRF-40 (1 ug/kg iv bolus) stimulates GH release within five minutes but does not elevate serum prolactin, TSH, LH or ACTH (measured indirectly through plasma cortisol), or blood glucose or plasma levels of 8 enteropancreatic hormones. When graded doses of hpGRF-40 (0.1 to 10 ug/kg) were given iv, no differences were noted in the maximum levels of serum GH achieved. Doses of 1, 3.3, and 10 ug/kg hpGRF-40 elicited a prolonged and biphasic pattern of GH release. Twenty-four hours after hpGRF-40 administration serum somatomedin C increased in 66% of subjects tested. Side effects included a feeling of warmth and facial flushing in 66% (3.3 ug/kg) and 100% (10 ug/kg) of men given hpGRF-40. hpGRF-40 (3.3 ug/kg iv) selectively stimulates GH release and somatomedin C production in normal women, although no differences were found in GH responsivity during the menstrual cycle. hpGRF-40 given subcutaneously and intranasally to normal men requires approximately 10 and 100 fold higher doses than the iv route to achieve similar stimulation. The calculated metabolic clearance rate of hpGRF-40 is $194\pm17.5$ $1/m^2/day$; the disappearance rate occurs as two phases: an initial equilibration phase of $7.6\pm1.2$ minutes and a subsequent elimination phase of $51.8\pm5.4$ minutes. Seven adults with idiopathic GH deficiency (IGHD) were given hpGRF-40 0.33 ug/kg iv every three hours for five days and then were rechallenged with 10 ug/kg iv. The GH response to subsequent challenge was greater and serum somatomedin C (mean$\pm$SE) increased significantly over the five-day period from $0.27\pm0.14$ to $0.89\pm0.29$ U/ml (normal $0.94\pm0.3$, mean$\pm1$ SD). Forty children with short stature were evaluated for GH reserve following pharmacological tests and after a single iv injection hpGRF-40 (3.3 ug/kg). The children were grouped into IGHD, organic hypopituitarism (OH), intrauterine growth retardation (IUGR), and constitutional delay of growth (CD) categories. In IGHD & OH patients' GH concentrations did not increase to more than 7 ng/ml (nanogram/ml) following pharmacologic stimulation. However, the mean ($\pm$SE) responses to hpGRF-40 were $3.4\pm1.1$ ng/ml and $8.2\pm2.4$ ng/ml in the OH and IGHD categories respectively. All children with IUGR, CD, and unclassified groups responded briskly to hpGRF-40 although there was wide variation of GH levels (5–25 ng/ml). Two GH deficient children were studied on constant diets and received hpGRF-40, 1 ug/kg q 3 h subcutaneously over 5 days. Both subjects demonstrated a reduction in nitrogen excretion and an increase in calcium excretion. Somatomedin C levels rose in both patients. Norleucine$^{27}$ hpGRF(1-29)-NH$_2$ markedly stimulated GH secretion at 0.1 ug/kg in normal young men. Studies suggest that GH deficiency in childhood often results from hypothalamic GHRH deficiency rather than pituitary disease. hpGRF-40 and its analogs may find therapeutic application of treatment of GH deficiency and in other disorders in which an increase or decrease in the secretion of GH would be beneficial.

The anabolic effects of GH include nitrogen (N) retention in association with hypercalcuria. hpGRF stimulates GH release in some GH deficient children. To study the therapeutic potential of hpGRF, hpGRF (1 ug/kg) was administered s.c. by Pulsamat pump [produced by Ferring Laboratories] for the last 6 days of a 16 day constant diet study period. Two short boys (8.3 & 9.6 yr), height ages (4.7 & 5.0 yr) and bone ages (5.5 & 3.5 yr) had low serum somatomedin C levels (0.13 & 0.05 U/ml) and subnormal peak GH responses to arginine/L-Dopa (5 & 1 ng/ml). Peak GH response to i.v. bolus hpGRF (3.3 ug/kg) were 12 & 20 ng/ml. In response to 6 days hpGRF therapy N excretion (mean$\pm$SE) fell in both children ($24.6\pm0.2$ to $20.6\pm0.6$ & $19.2\pm1.2$ to $15.2\pm0.6$ gm/gm creatinine; $p<0.05$). Urinary calcium increased in both children ($140\pm10$ to $200\pm10$ & $120\pm10$ to $210\pm20$; $p<0.01$). Somatomedin C levels increased markedly in one child and slightly in the other (0.13 to 0.56; & 0.02 to 0.08 U/ml). These children received a 6 month course of hpGRF therapy. This was administered in a dose of 1 microgram/kg body weight subcutaneously for approximately 2 months and then the dose was increased to 3.3 ug/kg body weight and these doses were each administered every 3 hours by Pulsamat pump. In each child acceleration of linear growth was demonstrated. The beneficial therapeutic potential of this mode of administration is obvious.

In general, GRF doses from 0.1 to 10 micrograms per kilogram body weight appear to be effective with those in the 1 ug per kilogram body weight preferred.

Administration of such doses about every half hour to about every 5 hours with doses of from 2½ to 3½ hours is preferred and every 3 hours 8 times per day most preferred. Dosage volumes of from 10 to 200 microliters for subcutaneous administration are suggested with from 25 to 75 preferred and 50 microliters most preferred. GRF and GH may be parenterally introduced including subcutaneously, intravenously and peritoneally.

Dosages should not be introduced faster than about 2 times the half life of the hormone in the blood of the subject and preferably at least about 3 times the half life.

The growth-stimulating compositions may be administered in a dynamic dosage on a pulsatile basis as above discussed via the apparatus disclosed in U.S. Pat. No. 4,397,639, the disclosure of which is hereby incorporated herein by reference. An alternative form of pulsed fluid administering apparatus (also referred to as an intermittent infusion pump) is shown in the drawing and includes a reservoir 10 which contains the composition to be administered in an appropriate concentration. The contents of reservoir 10 are administered to the subject via any suitable administration means 15, e.g., those considered above.

The fluid contents of reservoir 10 are delivered through the administering patient interface 15 via a gated pump 12. The pump 12 is activated when an appropriate level Boolean signal (e.g., "1" level) is applied to a control port ("C"). Most simply, the control port C may be activated by an oscillator having a fixed (or adjustable) repetition rate corresponding to the repetition rate desired for fluid administration. Such oscillators will typically have an unequal duty cycle with a much longer off time vis-a-vis its active period. Oscillators of such type are per se well known to those skilled in the art and may employ, for example, resistance/capacitance charge-trigger relaxation oscillator circuits or the like. Yet further, a microprocessor and an attendant memory may be employed and programmed to excite the pump 12 at appropriate times.

Correspondingly, flexible circuitry for actuating pump 12 is shown in the drawing and includes a master clock oscillator 18 supplying its output to the count input of a counter 21. A switch 22 is connected to the preset input of counter 21 to initialize the counter to a predetermined (e.g., cleared) state. Thereafter the counter 21 cycles through one complete sequence of states during each operational period, e.g., once per 24 hour day.

Output leads from each of the counter 21 stages are connected as inputs to a combinatorial circuit 23 which functions as a per se well known counter-state decoder. The outputs of decoder 23 become active during those state or states of counter 21 during which fluid delivery from reservoir 10 to the subject is desired. Finally, the individual outputs of decoder 23 are connected via an OR-logic gate 25 to the control port of pump 12. Accordingly, the apparatus of the drawing activates the pump 12 during those states of counter 21 during the overall one-day cyclical period when fluid is to be delivered to the subject.

The combinatorial network/decoder 23 may be of fixed construction to have a permanent time-pattern of fluid delivery times. Alternatively, the decoding pattern may be variable if it is desired from time to time to change the timing or duration of fluid delivery.

As can be seen from the foregoing, dynamic dosage is critical to the successful utilization of GRF and similarly of GH. The circadian rhythm is also critical to the utilization of GRF and GH. The levels of these hormones are found by some investigators to rise and fall in a daily cycle. To be physiologically mimetic a dynamic dosage of the GH or GRH following the pattern of release in normal subjects is indicated. However, each live subject and each patient will have different treatment objectives and presenting conditions leaving the final dosage determination to the specific circumstances of each case. For example, if animal growth is to be promoted, the administration would be to a normal animal presumably actively producing GRF and GH. In those humans suffering drawfism some will be GRF deficient and some GH deficient with partial deficiencies in each area possible.

It will be immediately obvious to those skilled in the art that many dynamic dosages of GH and GRF may be utilized and the foregoing is only exemplary and the invention will be limited only by the claims.

What is claimed is:

1. A method of therapeutically effective treatment of a living animal comprising administering to the animal a dynamic dosage of growth hormone releasing factor, analogs, biologically active fragments and derivatives thereof (collectively GRF) said dynamic dosage comprising administration of GRF to be interrupted by periods of non-administration of GFR of from at least about 2 times the half-life of GRF in the blood.

2. The method of claim 1 wherein the period of non-administration of GRF is at least about 3 times the half life of GFR in the blood.

3. The method of claim 1 wherein the GRF is administered subcutaneously.

4. The method of claim 1 wherein the GRF is administered chronically for a period in excess of 5 days.

5. The method of claim 1 wherein the animal is a human.

6. The method of claim 1 wherein the dynamic dosage per introduction is from about 0.1 to 10 micrograms per kilogram of body weight.

7. The method of claim 6 wherein the dynamic dosage is from 1 microgram to 3.3 micrograms per kilogram.

8. The method of claim 6 wherein the GRF is nor-leucine[27] hpGRF(1-29)-$NH_2$.

9. The method of claim 1 wherein the dynamic dosage is administered by intermittent infusion pump.

10. A method of therapeutically effective treatment of a living animal comprising administering to the animal a dynamic dosage of growth hormone releasing factor, analogs, biologically active fragments and derivatives thereof (collectively GRF) said dynamic dosage comprising administration of GRF from about every half hour to about every 5 hours.

11. The method of claim 10 wherein the administration of GRF is from about every two and one-half hours to about every three and one-half hours.

12. The method of claim 10 wherein the GRF is administered subcutaneously.

13. The method of claim 10 wherein the GRF is administered chronically for a period in excess of 5 days.

14. The method of claim 10 wherein the animal is a human.

15. The method of claim 10 wherein the dynamic dosage per introduction is from 0.1 to 10 micrograms per kilogram of body weight.

16. The method of claim 15 wherein the dynamic dosage is from 1 microgram to 3.3 micrograms per kilogram.

17. The method of claim 10 wherein the dynamic dosage per introduction is from 0.1 to 10 micrograms per kilogram body weight.

18. The method of claim 17 wherein the dynamic dosage is from 1 microgram to 3.3 micrograms per kilogram.

19. The method of claim 14 wherein the GRF is norleucine[27] hpGRF(1-29)-$NH_2$.

20. The method of claim 14 wherein the administration of GRF is from about every two and one-half hours to about every three and one-half hours.

21. The method of claim 20 wherein the dynamic dosage per introduction is from 0.1 to 10 micrograms per kilogram of body weight.

22. The method of claim 21 wherein the GRF is administered subcutaneously chronically for a period in excess of five days by intermittent infusion pump.

23. The method of claim 22 wherein the GRF is norleucine[27] hpGRF(1-29)-$NH_2$.

24. The method of claim 10 wherein the dynamic dosage is administered by intermittent infusion pump.

25. A method of therapeutically effective treatment of a living animal comprising administering to the animal a dynamic dosage of growth hormone, analogs, biologically active fragments and derivatives thereof (collectively GH) said dynamic dosage comprising administration of GH to be interrupted by periods of non-administration of GH of from at least about two times the half-life of GH in the blood.

26. The method of claim 25 wherein the GH is administered chronically for a period in excess of 5 days.

27. The method of claim 25 wherein the dynamic dosage is administered by intermittent infusion pump.

28. A method of therapeutically effective treatment of a living animal comprising administering to the animal a dynamic dosage of growth hormone, analogs, biologically active fragments and derivatives thereof (collectively GH) said dynamic dosage comprising administration of GH about every half hour to about every 5 hours.

29. The method of claim 28 wherein the dynamic dosage is administered by intermittent infusion pump.

30. A method of diagnosing in a living animal growth retardation due to the inability of the pituitary to respond to a dynamic dosage of growth hormone releasing factor, analogs, biologically active fragments and derivatives thereof (collectively GRF) wherein the dynamic dosage of GRF comprises administration of GRF from about every half hour to about every 5 hours the method comprising administering said dynamic dosage and measuring the response thereto.

* * * * *